United States Patent [19]

McElveen, Jr. et al.

[11] Patent Number: 5,163,922

[45] Date of Patent: Nov. 17, 1992

[54] DUAL-VALVED CONNECTOR FOR INTRAVENOUS SYSTEMS

[75] Inventors: Charles E. McElveen, Jr., 2322LA Vista Dr., #15, Burlington, N.C. 27215, George F. Arp, Rochester, N.Y.

[73] Assignee: Charles E. McElveen, Jr., Burlington, N.C.

[21] Appl. No.: 693,969

[22] Filed: Apr. 29, 1991

[51] Int. Cl.⁵ ............................................. A61M 5/00
[52] U.S. Cl. .................................... 604/249; 604/83; 604/905; 251/149.1
[58] Field of Search ............................ 604/33, 82-83, 604/85-86, 236, 244, 249, 905; 137/605; 251/149.1

[56] References Cited

U.S. PATENT DOCUMENTS

| | | |
|---|---|---|
| 3,409,015 | 11/1968 | Swanson . |
| 3,438,554 | 4/1969 | Schwartzman . |
| 3,570,484 | 3/1971 | Steer et al. ........................ 604/249 |
| 3,799,171 | 3/1974 | Patel . |
| 3,800,799 | 4/1974 | McWhorter . |
| 4,416,273 | 11/1983 | Grimes . |
| 4,432,764 | 2/1984 | Lopez . |
| 4,620,648 | 11/1986 | Schwartzman . |
| 4,693,623 | 9/1987 | Schwartzman . |
| 4,745,950 | 5/1988 | Mathieu ........................ 137/798 |
| 4,886,507 | 12/1989 | Patton et al. . |
| 4,915,687 | 4/1990 | Sivert . |
| 5,064,416 | 11/1991 | Newgard et al. ............... 604/167 |

FOREIGN PATENT DOCUMENTS 9001352  2/1990  World Int. Prop. O. ............ 604/83

OTHER PUBLICATIONS

*American Jrnl. of Nursing*, Feb. 1991, p. 70, Dimensional Sheet, Dab-O-Matic Corporation, Mt. Vernon, N.Y.

Primary Examiner—C. Fred Rosenbaum
Assistant Examiner—C. Maglione
Attorney, Agent, or Firm—Eugene Stephens & Associates

[57] ABSTRACT

A connector provides access to intravenous fluid lines, bags, and vials with either conventional needles or needleless fittings. The connector has a housing with at least one input port and an output port. Two valves normally biased to closed positions control passage of fluid between the one input port and the output port, One of the valves is displaceable to an open position by a needleless fitting, and the other valve is displaceable to an open position by a conventional needle.

19 Claims, 5 Drawing Sheets

DUAL-VALVED CONNECTOR FOR INTRAVENOUS SYSTEMS

BACKGROUND

Each year there are as many as six hundred thousand reported injuries nationwide to health care professionals from needle sticks. Many of these sticks occur from needles used for making connections to intravenous fluid lines or bags or for transferring medicants from one vial to another. Because of associated risks of serious infection, hospitals are required to conduct an examination of each such injury by needle stick and to perform expensive screening of the injured for such diseases as hepatitis and AIDS. Some localities also require hospitals to administer expensive prophylactics such as AZT to injured health care professionals on request.

For these reasons, many in the health care field are now advocating the elimination of needles, also referred to as "sharps", from all nonessential medical uses. Although alternatives to needles for making connections to intravenous fluid lines, bags, and vials are now available, acceptance of these alternatives has been slowed by difficulties with making such a radical transition from long-established practices and standards involving needles.

One alternative is a needleless injection port arrangement described in recently issued U.S. Pat. No. 4,915,687 to Sivert. The arrangement includes a valve that is displaceable by a needleless tip of a syringe for opening a passageway in an injection port to an intravenous fluid line. The displaceable valve of Sivert replaces a conventional valve made from a self-sealing elastomeric material that is penetrable by a needle for opening a passageway through a similar injection port.

Although valved connections like Sivert's appear to provide an effective replacement for the conventional elastomeric valves of present intravenous systems, such a changeover to needleless connections is expected to take many years to complete. In addition, interim incompatibilities between the different connections may cause considerable confusion and increase cost to hospitals by requiring duplication of certain inventories to ensure accessibility of intravenous fluid lines, bags, and vials.

SUMMARY OF INVENTION

Our invention is intended to facilitate the change from needle-accessible to needleless connections for intravenous fluid lines, bags, and vials. This is accomplished by a dual-valved connector that can be formed as a part of an intravenous fluid line, bag, or cover for medical vials or as a stand-alone component for assembly in an intravenous fluid related system. The dual-valved connector is primarily intended to provide an alternative to conventional needles for accessing intravenous fluid lines, bags, and vials. However, if appropriate needleless fittings are not available or if other such incompatibilities arise, the connector also permits access to the intravenous lines, bags, and vials by conventional needles.

The dual-valved connector is assembled within a housing having an input port and an output port. A first valve is disposed within the housing for opening and closing a first fluid passageway between the input and output ports. A second valve is carried by a movable portion of the first valve for opening and closing a second fluid passageway between the input and output ports. Normally, both valves are biased into closed positions. However, the first valve is displaceable to an open position by a needleless fitting inserted into the input port, and the second valve is displaceable to an open position by a conventional needle inserted into the same input port without displacing the first valve to an open position.

The first valve preferably includes a valve seat formed in the housing surrounding the input port and a valve head carried on one end of a resilient member that urges the valve head against the valve seat. The resilient member is supported within the housing and includes a hollow portion that is aligned with the input port. The second valve is preferably made as an elastomeric plug carried within an opening in the valve head in alignment with both the input port and the hollow portion of the resilient member.

The valve head of the first valve is displaceable by a needleless fitting inserted into the input port. However, the elastomeric plug is penetrable by a conventional needle without displacing the valve head in which the plug is carried. That is, the resilient member exerts a first force, urging the valve head against the valve seat, that is greater than a second force exerted by the plug in resistance to penetration by the conventional needle. Both the opening in the valve head and the hollow portion of the resilient member are aligned with the input port so that the conventional needle can pass through the elastomeric plug into the housing without further obstruction.

DRAWINGS

DETAILED DESCRIPTION

Figure 1:
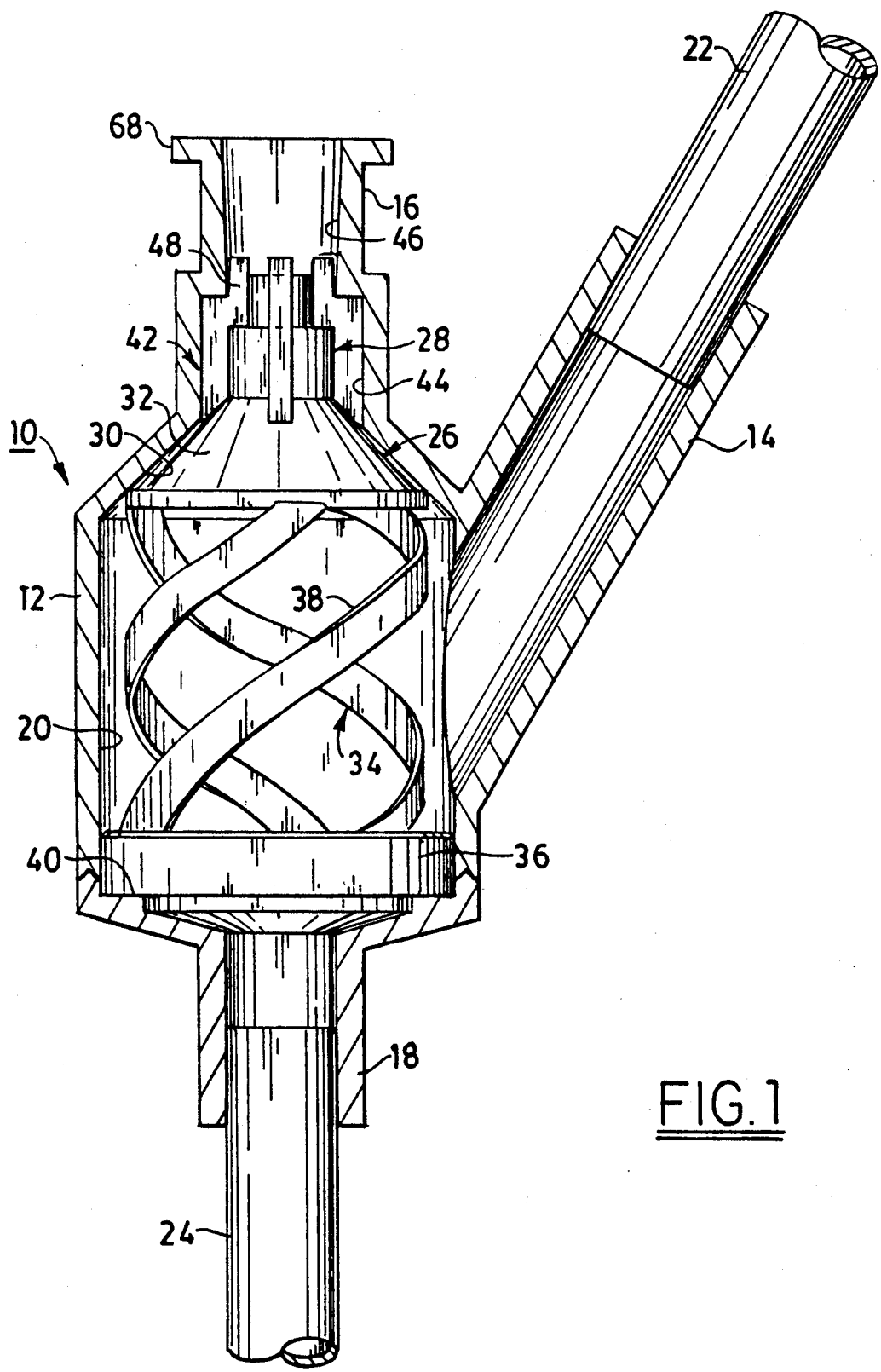
FIG. 1 is an enlarged view partly in cross section through our dual-valved connector arranged as a "Y-shaped" junction of an intravenous fluid line.
Figure 2:
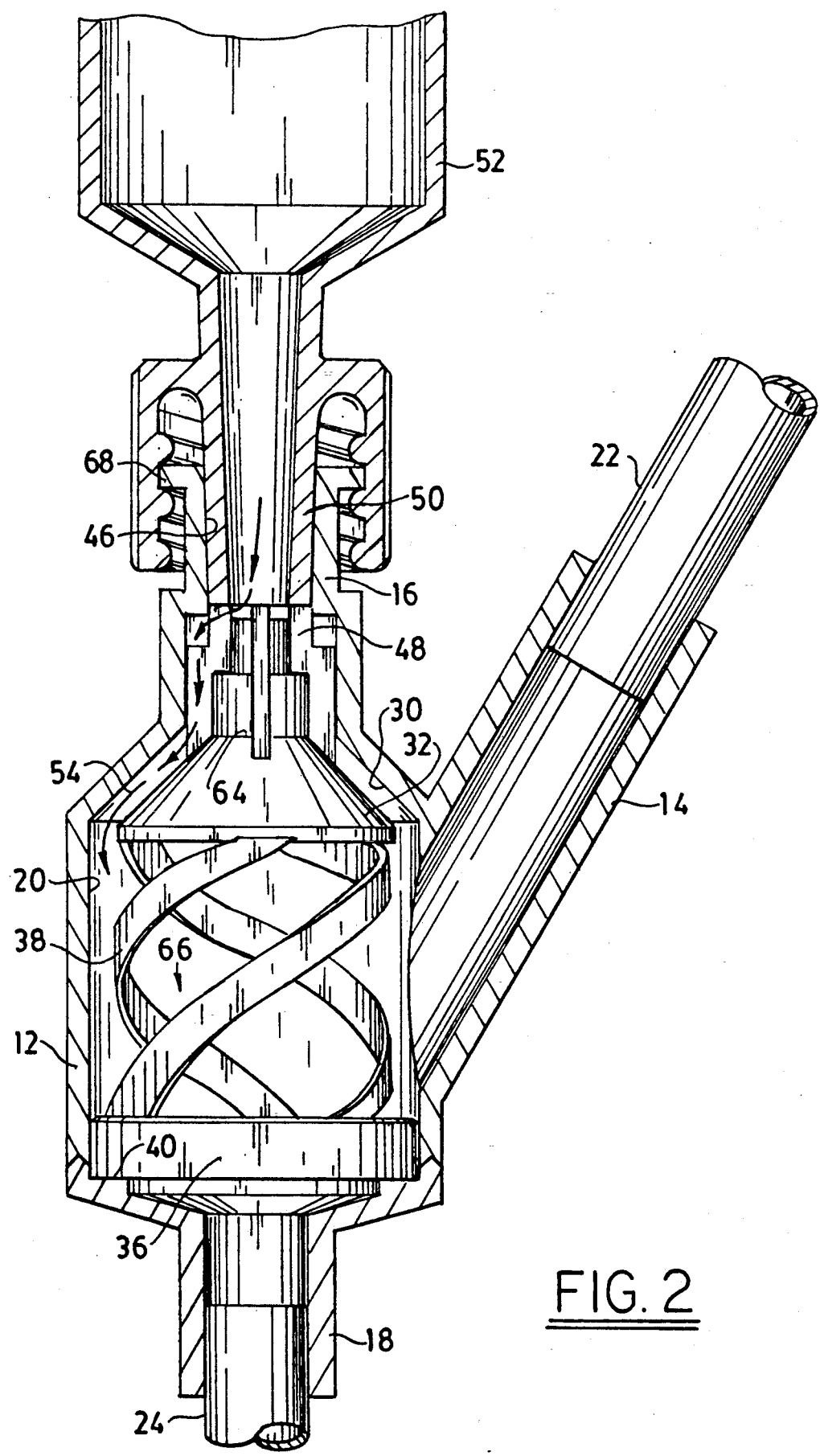
FIG. 2 is a similar view of the same connector engaged by a needleless fitting of a syringe.
Figure 3:
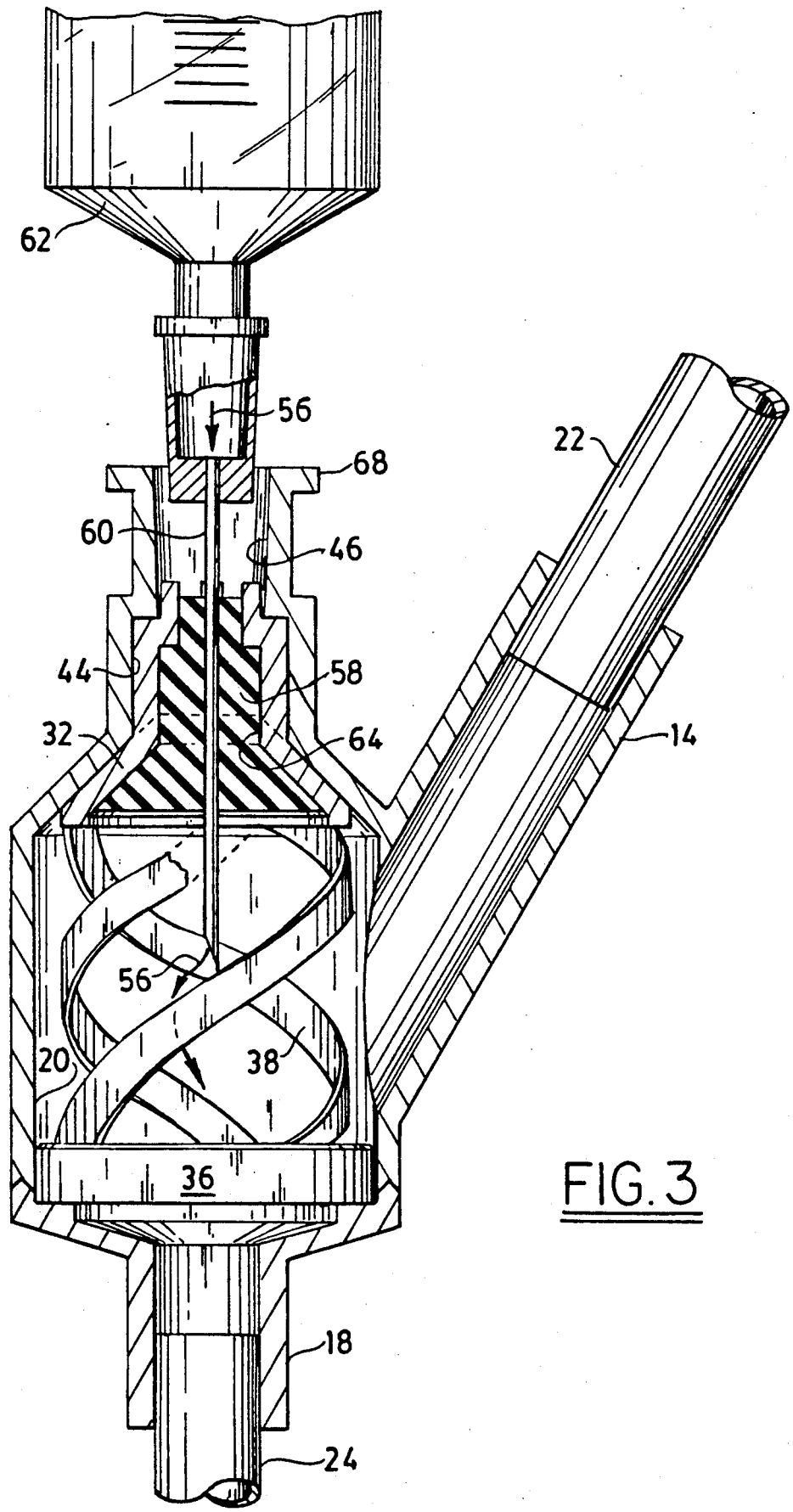
FIG. 3 is another similar view but the same connector is engaged by a conventional needle mounted on a syringe.

Our dual-valved connector 10 is shown in FIGS. 1 through 3 as a "Y-shaped" junction formed along an intravenous fluid line. The connector 10 includes a housing 12 having two input ports 14 and 16 connected to a single output port 18 through a chamber 20. The input port 14 and the output port 18 interconnect portions 22 and 24 of an intravenous fluid line in open fluid communication with each other through the chamber 20.

However, fluid communication between the input port 16 and output port 18 is controlled by two valves 26 and 28 that open and close respective passageways between the input port 16 and chamber 20. The valve 26 includes a valve seat 30 that is formed by a portion of the chamber 20 surrounding the input port 16 and a valve head 32 that is formed integrally with a resilient member 34 for biasing the valve head 32 against the valve seat 30. The resilient member 34 includes, in addition to the valve head 32, a base ring 36 and a multi-helix coil spring 38 interconnecting the valve head 32 and base ring 36.

The housing 12 is made in two pieces to permit assembly of the resilient member 34 within the chamber 20. The valve seat 30 is formed in one of the two pieces at one end of the chamber 20 for receiving the valve head 32 of the resilient member, and an annular land 40 is formed in the other of the two pieces at the other end of the chamber 20 for supporting the base ring 36 of the resilient member. The valve seat 30 and annular land 40 are spaced apart through a distance that partially compresses the coil spring 38 and urges the valve head 32 against the valve seat 30 as shown in FIG. 1.

The resilient member 34 also includes evenly spaced guide posts 42 that project from the valve head 32 into inner bore 44 and outer bore 46 of the input port 16. The inner bore 44 cooperates with the guide posts 42 for aligning the valve head 32 to the valve seat 30. With particular reference to FIG. 2, it can be seen that the outer bore 46 is formed with a taper that is dimensioned to seat a conventional needlefree fitting 50 formed by a frusto-conical exit tip of a syringe 52 or other medicinal-dispensing article. Stepped portions 48 of the guide posts 42 extend into the outer bore 46 for engaging the needlefree fitting 52 before the fitting is seated against the outer bore 46. The engagement of the needlefree fitting 52 with the guide posts 42 displaces the valve head 32 from the valve seat 30 and opens a first fluid passageway 54 between the input port 16 and the output port 18.

The other valve 28, best seen in FIG. 3, controls a second fluid passageway 56 between the input port 16 and the output port 18. At least part of the second fluid passageway 56 operates in parallel with the first fluid passageway 54 for separately connecting the input port 16 to the chamber 20. However, the remaining parts of the two passageways between the chamber 20 and output port 18 are contiguous.

Figure 4:
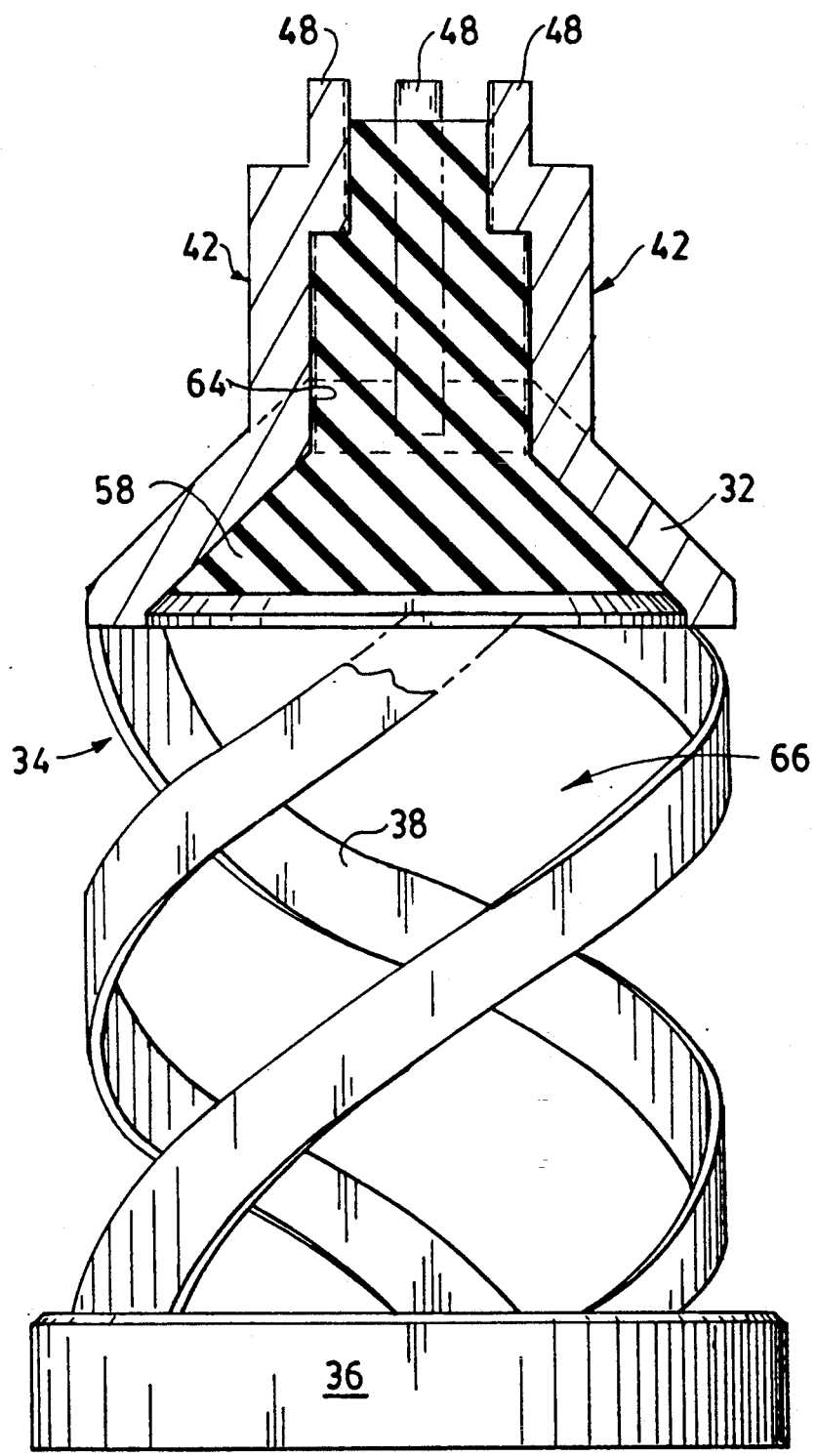
FIG. 4 is a further enlarged cross-sectional view of a resilient member and an elastomeric plug that are used together within the connector.

The parallel portion of the second fluid passageway 56 extends through the valve head 32 but is interrupted by an elastomeric plug 58 also shown in FIG. 4 within the enlarged view of resilient member 34. The elastomeric plug 58 is fitted within the valve head 32 and extends through an opening 64 in the valve head between the guide posts 42 for closing the second fluid passageway 56. However, the elastomeric material is preferably the same self-sealing, non-coring material that is regularly used in conventional injection ports. Accordingly, the elastomeric material can be penetrated by a conventional needle 60 of syringe 62 for opening the second fluid passageway 56 through the valve head 32.

The coil spring 38 of the resilient member includes a hollow portion 66 that provides a large open space within the chamber 20. Both the hollow portion 66 of the resilient member and the opening 64 in the valve head are aligned with the input port 16 so that when the conventional needle 60 is inserted into the input port 16, the needle 60 can pass through the elastomeric plug 58 into the chamber 20 without further obstruction. In fact, the hollow portion 66 continues through the base ring 36 so that the needle 60 can pass without obstruction from one end to the other of chamber 20.

Although the elastomeric plug 58 of valve 28 is carried on the valve head 32 of valve 26, the valve 28 operates independently of the valve 26. The coil spring 38 of the resilient member exerts a force through the valve head 32 against the valve seat 30 that is greater than a force exerted by the elastomeric plug 58 in opposition to penetration by the conventional needle 60. Accordingly, the valve head 32 is not displaced from the valve seat 30 by the penetration of the elastomeric plug 58 by the conventional needle 60. This assures that the valve 26 remains closed while the valve 28 is open to prevent any leakage of air or contaminants into the chamber 20 through the passageway 54.

Figure 5:
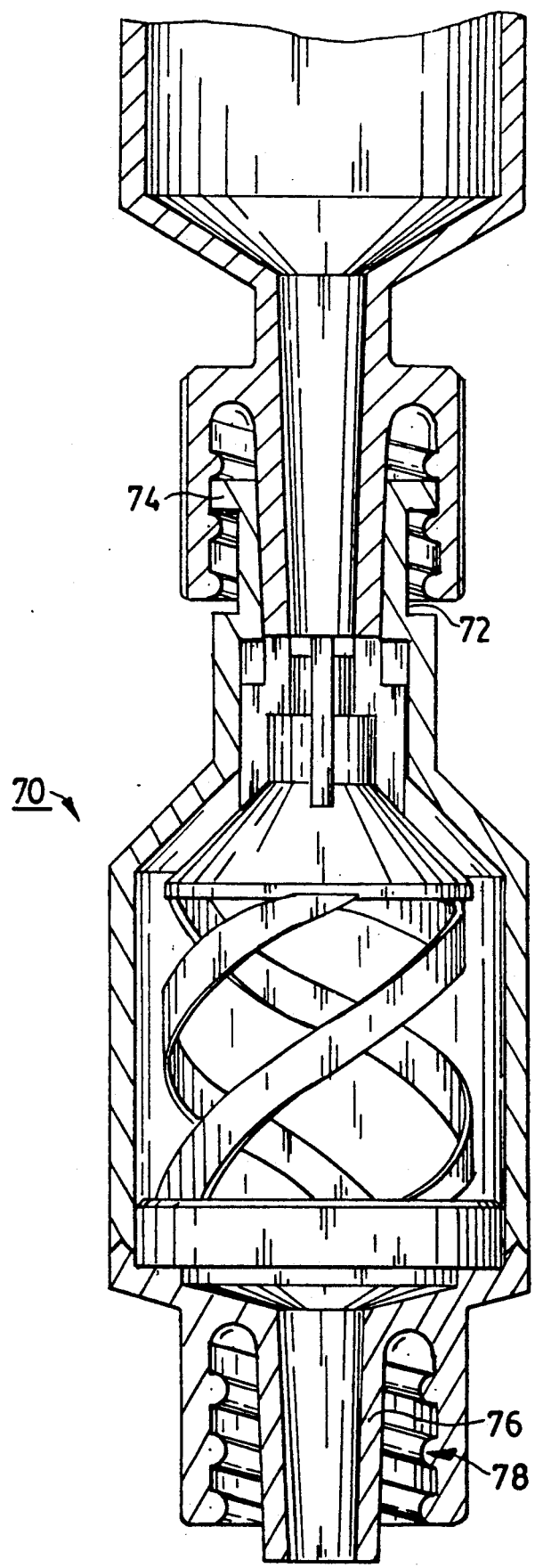
FIG. 5 is an enlarged view partly in cross section of our dual-valved connector arranged as a stand-alone component that can be assembled as a part of an intravenous line.

The input port 16 of connector 10 is also shown with a threaded rim 68 for making threaded connections to conventional fittings used in intravenous lines. Similarly, input port 72 of stand-alone connector 70 shown in FIG. 5 also includes a threaded rim 74. However, output port 76 of the connector 70 includes a mating threaded fitting 78 for assembling the connector as an alternative component of an intravenous system. The fittings 74 and 78 may be of a type presently sold under the tradename LUER-LOC by Becton Dickinson of Franklin Lakes, N.J.

Although not further illustrated, it will be apparent to those of skill in the art that our dual-valved connector can also be adapted for making a variety of other connections for intravenous systems. For example, the connector could be incorporated in a cover of a medicinal vial or could be made as an injection port of a intravenous bag that is connected to the distal end of an intravenous line. It would also be possible to substitute other parts from those specifically illustrated. For example, instead of using a coil spring to close one of the valves, interleaved disk springs could be used for the same purpose. However, such a substitute spring may require appropriate perforation so as not to interrupt flow through the connector.

Component parts of both illustrated connectors 10 and 70 are preferably made from injection molded resin that is chemically inert to the environment of its anticipated use. The components should also be sterile. Accordingly, a threaded cap (not shown) could be used to cover the input ports 16 and 72 prior to use.

We claim:

1. A dual-valve connector for use with both conventional needles and needleless fittings of intravenous systems comprising:
   a housing having input and output ports;
   first and second fluid passageways separately interconnecting said input and output ports;
   a first valve disposed within said housing for opening and closing said first fluid passageway between said input and output ports; and
   a second valve carried by a movable portion of said first valve for opening and closing said second fluid passageway between said input and output ports,
   wherein said first valve is displaceable to an open position by inserting a needleless fitting into said input port, and said second valve is displaceable to an open position by inserting a conventional needle into said input port without displacing said first valve to an open position.

2. The connector of claim 1 in which said first valve is biased to a closed position by a resilient member.

3. The connector of claim 2 in which said second valve includes a plug that is penetrable by the conventional needle inserted into said input port for opening said second fluid passageway.

4. The connector of claim 3 in which said resilient member exerts a force for biasing said first valve to a closed position that is greater than a force exerted by said plug in resistance to penetration by the conventional needle.

5. The connector of claim 4 in which said resilient member includes a hollow portion aligned with said input port.

6. The connector of claim 5 in which said input port includes a fitting that is threadably engageable with the needleless fitting inserted into the input port.

7. The connector of claim 6 in which said output port includes a fitting of a type that is threadably engageable with the fitting associated with the input port.

8. A connector for accessing intravenous systems with either a conventional needle or a needleless fitting comprising:
- a housing having input and output ports interconnected by a chamber;
- a resilient member mounted within said chamber and having a hollow portion aligned with said input port;
- a valve seat defined within said chamber;
- a valve head carried on one end of said resilient member and biased by said resilient member against said valve seat; and
- a plug carried within an opening in said valve head in alignment with said input port,
- wherein said valve head is displaceable from said valve seat by inserting the needleless fitting into said input port, and said plug is penetrable by inserting the conventional needle through said input port into said chamber.

9. The connector of claim 8 in which said valve head is formed integrally with said resilient member.

10. The connector of claim 9 in which said plug is surrounded by guide posts projecting from said valve head for engaging the needleless fitting inserted into said input port.

11. The connector of claim 10 in which said resilient member exerts a force for biasing said valve head against said valve seat that is greater than a force exerted by said plug in resistance to penetration by the conventional needle.

12. The connector of claim 11 in which said input port includes a fitting that is threadably engageable with the needleless fitting inserted into the input port.

13. In a needleless injection port arrangement for an intravenous fluid system including:
- a housing having an input port connected to an output port through a chamber;
- a resilient member supported within said chamber;
- a valve seat formed in said chamber surrounding said input port; and
- a valve head carried on one end of said resilient member, biased by said resilient member against said valve seat, but displaceable from said valve seat by a needleless fitting inserted into said input port for opening a first fluid passageway between said input port and said chamber, the improvement in which said valve head includes a plug that is penetrable by a conventional needle inserted through said input port into said chamber for opening a second fluid passageway between said input port and said chamber.

14. The injection port arrangement of claim 13 in which said resilient member includes a hollow portion aligned with said input port.

15. The injection port arrangement of claim 14 in which said valve head includes an opening for mounting said plug, and said opening is also aligned with said input port.

16. The injection port arrangement of claim 15 in which said resilient member exerts a force for biasing said valve head against said valve seat that is greater than a force exerted by said plug in resistance to penetration by the conventional needle.

17. The injection port arrangement of claim 16 in which said valve head is formed integrally with said resilient member.

18. The injection port arrangement of claim 17 in which said resilient member includes an integrally formed multiple helix coil spring for biasing said valve head against said valve seat.

19. The injection port arrangement of claim 18 in which said input port includes a fitting that is threadably engageable with the needleless fitting inserted into the input port.

* * * * *